US00PP28710P3

(12) United States Plant Patent
Klemm et al.

(10) Patent No.: US PP28,710 P3
(45) Date of Patent: Nov. 28, 2017

(54) ***PELARGONIUM* PLANT NAMED 'KLEPS15376'**

(50) Latin Name: *Pelargonium grandiflorum*
Varietal Denomination: KLEPS15376

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 73 days.

(21) Appl. No.: 14/998,947

(22) Filed: Mar. 9, 2016

(65) Prior Publication Data

US 2017/0265361 P1 Sep. 14, 2017

(51) Int. Cl.
*A01H 5/02* (2006.01)

(52) U.S. Cl.
USPC ..... Plt./324

(58) Field of Classification Search
USPC ..... Plt./324
See application file for complete search history.

*Primary Examiner* — Anne M Grunberg
(74) *Attorney, Agent, or Firm* — Barbara Campbell; Bethany R. Roahrig; Cochran Freund & Young, LLC

(57) ABSTRACT

A new *pelargonium* plant particularly distinguished by purple-red flowers with dark-purple eyes and an upright, round, and bushy habit, is disclosed.

1 Drawing Sheet

Genus and species: *Pelargonium grandiflorum.*
Variety denomination: 'KLEPS15376'.

BACKGROUND OF THE NEW PLANT

The present invention comprises a new and distinct variety of *pelargonium*, botanically known as *Pelargonium grandiflorum* and hereinafter referred to by the variety name 'KLEPS15376'. 'KLEPS15376' originated from a cross-combination in August 2010 in Stuttgart, Germany between the proprietary female *pelargonium* variety 'PSH-2009-C-Dark-Red' (unpatented) and the proprietary male *pelargonium* variety 'PS-2006-0001' (unpatented).

Seeds from the cross-combination in Stuttgart, Germany were obtained. The seeds were sown and plants were grown for evaluation. A single plant was selected in June 2011 and subsequently named 'KLEPS15376'. In August 2011 'KLEPS15376' was first vegetatively propagated by vegetative cuttings from stems and branches. 'KLEPS15376' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Purple-red flowers with dark-purple eyes; and
2. An upright, round, and bushy habit.

DESCRIPTION OF THE PHOTOGRAPH

This new *pelargonium* plant is illustrated by the accompanying photograph which shows an overall view of the plant. The photograph is of an approximately ten-week-old plant grown in Stuttgart, Germany under greenhouse conditions in April 2014. The colors shown are as true as can be reasonably obtained by conventional photographic procedures.

DESCRIPTION OF THE NEW VARIETY

The following detailed descriptions set forth the distinctive characteristics of 'KLEPS15376'. The data which define these characteristics were collected from asexual reproductions carried out in Stuttgart, Germany. Data was collected on five-month old plants in Stuttgart, Germany under greenhouse conditions in July 2015. Color references are to The R.H.S. Colour Chart of The Royal Horticultural Society of London (R.H.S.), 5$^{th}$ edition (2007).

Classification:
- *Family.*—Geraniaceae.
- *Botanical.*—*Pelargonium grandiflorum.*
- *Common.*—*Pelargonium*
- *Designation.*—'KLEPS15376'.

Parentage:
- *Female parent.*—The proprietary female *pelargonium* variety 'PSH-2009-C-Dark-Red' (unpatented).
- *Male parent.*—The proprietary male *pelargonium* variety 'PS-2006-0001' (unpatented).

Plant:
- *Form.*—Bushy and round.
- *Habit.*—Upright.
- *Height.*—25.0 cm.
- *Width.*—23.0 cm.
- *Natural flowering season.*—Spring to autumn.
- *Propagation type.*—Vegetative cuttings.
- *Time to produce a finished flowering plant.*—4 to 5 months.
- *Time to initiate and develop roots.*—28 days.
- *Root description.*—RHS 27D and fine.

Stems:
- *Quantity of stems per plant.*—5 to 6.
- *Color.*—RHS 137A.

*Surface texture*.—Moderately pubescent.
*Stem form*.—Round.
*Diameter*.—0.7 cm.
*Length*.—5.0 cm to 8.0 cm.
*Internode length*.—1.0 cm to 1.5 cm.
*Anthocyanin*.—Absent.

Leaves:
*Arrangement*.—Alternate.
*Shape*.—Cordate.
*Apex*.—Acute.
*Base*.—Open.
*Margin*.—Crenate.
*Surface texture*.—Upper surface: Smooth to sparsely pubescent. Lower surface: Smooth.
*Length*.—4.5 cm.
*Width*.—4.0 cm.
*Color*.—Upper surface: RHS 137B. Lower surface: RHS 137D.
*Petiole*.—Length: 5.0 cm to 8.0 cm. Diameter: 0.2 cm. Color: RHS 137A. Strength: Medium.
*Venation pattern*.—Palmate.
*Venation color*.—Upper surface: RHS 137D. Lower surface: RHS 138B.

Inflorescence:
*Lastingness of flowers on the plant*.—8 to 10 days.
*Umbels*.—Quantity of umbels per plant: 6. Length: 5.0 cm. Diameter: 5.0 cm.
*Individual florets of the umbel*.—Quantity of florets per umbel: 3 to 6. Depth: 2.5 cm. Diameter: 4.0 cm.
*Fragrance*.—Absent.

Flower buds:
*Cluster shape*.—Round.
*Cluster size*.—Length: 1.0 cm to 1.5 cm. Width: 1.0 cm to 1.5 cm.
*Surface texture*.—Smooth to moderately pubescent.
*Bud*.—Height: 0.5 cm to 1.0 cm. Width: 0.5 cm. Shape: Elliptic. Apex: Acute. Base: Obtuse. Margin: Rough. Color: RHS 137B.

Petals:
*Quantity per flower*.—5 to 6.
*Shape*.—Drop-shaped.
*Apex*.—Round.
*Base*.—Obtuse.
*Margin*.—Entire.
*Length*.—3.0 cm.
*Width*.—1.0 cm to 1.5 cm.
*Surface texture*.—Upper surface: Smooth. Lower surface: Smooth.
*Color of lobes*.—Upper lobes: Upper surface: RHS 61A around the border and about 0.5 cm wide and RHS N79A eyes on each lobe. Lower surface: RHS N74A around the border and about 0.5 cm wide and RHS N79B eyes on each lobe. Lower lobes: Upper surface: RHS N74A around the border and about 1.0 cm wide and RHS N79B eyes on each lobe. Lower surface: RHS N74A around the border and about 1.0 cm wide and RHS N79C eyes on each lobe.

Petaloids: Absent.

Sepals:
*Number per flower*.—5.
*Shape*.—V-shaped.
*Apex*.—Cuspidate.
*Base*.—Obtuse.
*Margin*.—Entire.
*Surface texture*.—Upper surface: Smooth. Lower surface: Moderately pubescent.
*Color*.—Upper surface: RHS 137C. Lower surface: RHS 137B.
*Length*.—1.2 cm.
*Width*.—0.5 cm.

Pedicel:
*Length*.—2.0 cm.
*Diameter*.—0.1 cm.
*Color*.—RHS 137B and RHS 177C.
*Surface texture*.—Moderately pubescent.
*Strength*.—Medium.

Peduncle:
*Length*.—5.0 cm to 7.0 cm.
*Diameter*.—0.2 cm.
*Color*.—RHS 137A.
*Surface texture*.—Moderately pubescent.
*Strength*.—Medium.

Reproductive organs:
*Stamens*.—Quantity of stamens per flower: Greater than 5. Anther length: 0.2 cm. Filament length: 0.8 cm. Filament color: RHS 71A. Pollen amount: Moderate. Pollen color: RHS 73B.
*Pistils*.—Number: 1. Stigma color: RHS 71A. Style length: 1.2 cm. Style color: RHS 71A. Ovary arrangement: Central. Ovary color: RHS 137D. Ovary diameter: 0.1 cm. Ovary length: 0.15 cm.

Fruit and seed set: None observed.

Disease and pest/insect resistance: None observed.

COMPARISON WITH PARENTAL LINES AND KNOWN VARIETY

'KLEPS15376' is distinguished from its parents as described in Table 1:

TABLE 1

Comparison with Parental Lines

| Characteristic | 'KLEPS15376' | Female parent 'PSH-2009-C-Dark-Red' | Male Parent 'PS-2006-0001' |
|---|---|---|---|
| Flower color | Purple-red with dark-purple eyes | Bright red with dark-red eyes | Dark-purple |
| Flower size | Medium | Medium | Small |

'KLEPS15376' can be compared to the commercial variety 'Camvio' (U.S. Plant Pat. No. 20,421), also commercially known as CANDY FLOWERS 'Violet Regal'. Differences between the two varieties are described in Table 2:

TABLE 2

Comparison with Similar Variety

| Characteristic | 'KLEPS15376' | Commercial line 'Camvio' |
|---|---|---|
| Flower color | Purple-red with dark-purple eyes | Neon-violet with dark-eyes |

We claim:

1. A new and distinct variety of *pelargonium* plant named 'KLEPS15376' as illustrated and described herein.

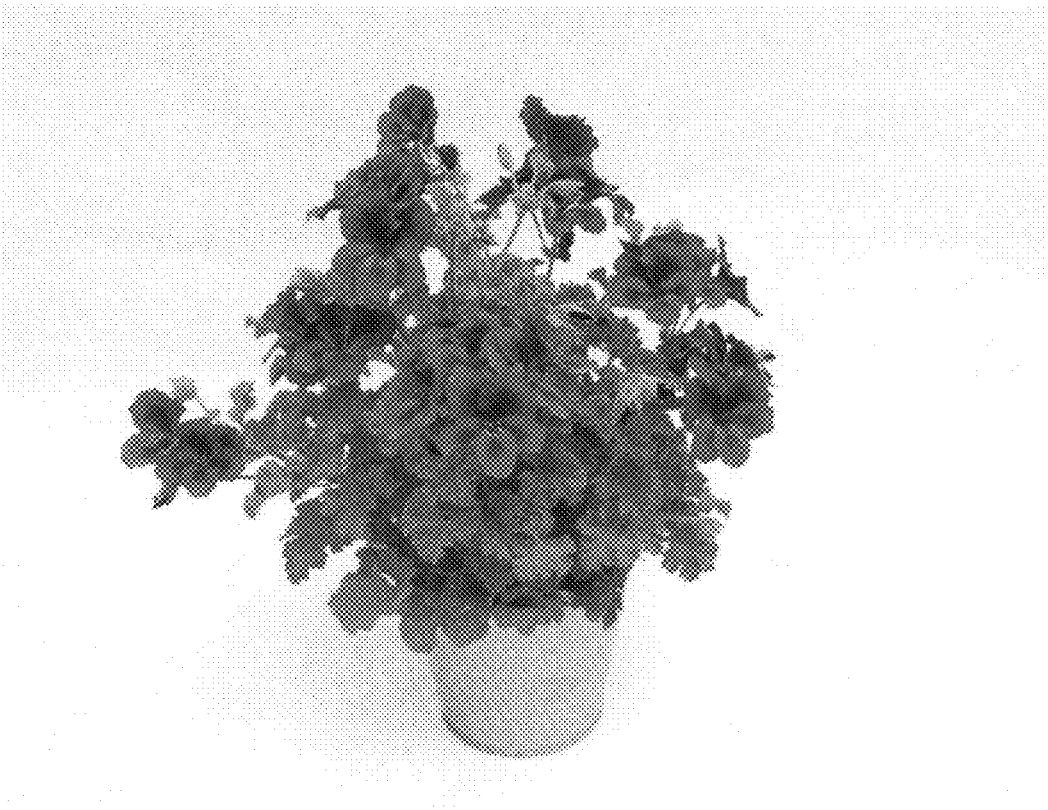

* * * * *